United States Patent [19]
Mauze et al.

[11] Patent Number: 5,142,155

[45] Date of Patent: Aug. 25, 1992

[54] CATHETER TIP FLUORESCENCE-QUENCHING FIBER OPTIC PRESSURE SENSOR

[75] Inventors: Ganapati R. Mauze, Sunnyvale; William F. Carlsen, Jr., Woodside, both of Calif.

[73] Assignee: Hewlett-Packard Company, Palo Alto, Calif.

[21] Appl. No.: 667,701

[22] Filed: Mar. 11, 1991

[51] Int. Cl.$^5$ .............................................. G01N 21/64
[52] U.S. Cl. .............................. 250/458.1; 250/227.23
[58] Field of Search ............ 250/458.1, 459.1, 227.23; 128/634, 664, 667, 673, 675

[56] References Cited

U.S. PATENT DOCUMENTS 4,476,870  10/1984  Peterson et al. ................... 128/634
4,994,396   2/1991  Lefkowitz et al. ............... 250/359.1

Primary Examiner—Constantine Hannaher
Assistant Examiner—Edward J. Glick

[57] ABSTRACT

A fiber optic pressure sensor suitable for use in measuring, for example, arterial blood pressure, is taught. A catheter tip is formed utilizing the phenomena of collision quenching or Foerster energy transfer quenching of fluorescence in order to measure the pressure exerted by the medium in which the sensors are placed. When utilizing a collision-quenching type of sensor, the change in concentration of a quencher is measured, the quencher being enclosed in the sensor tip, which is in hydrodynamic equilibrium with its ambient environment. Foerster-quenching type sensors measure the change in distance between the quencher and the fluorophore, which in turn are caused by pressure changes caused by the ambient environment in which the sensor is placed.

8 Claims, 4 Drawing Sheets

CATHETER TIP FLUORESCENCE-QUENCHING FIBER OPTIC PRESSURE SENSOR

INTRODUCTION

1. Technical Field

This invention pertains to catheter tip pressure sensors useful, for example, for measurement of blood pressure at a specified internal location of a patient.

2. Background

It is well known that a patient's blood pressure is an important indication of the well-being of the patient. More specifically, blood pressure at a specific location within the patient, for example, within a radial artery, gives a more specific indication of the well-being of the patient.

*Measurements in Medical Practice in Research*, Tsilik, and Halperin, *Sensors*, July 1987, pp. 11–17, describes certain prior art blood pressure measuring devices. One such prior art blood measurement device includes an electrical strain gauge activated in response to the pressure on a liquid column acting against a diaphragm, as applied via a disposable dome. While such a configuration is somewhat complex, it allows sufficient accuracy for most clinical applications. However, if the device is not manufactured properly, its accuracy is adversely affected, causing it to be unsuitable for use in biomedical research applications. In addition to the relative complexity, this type of prior art pressure sensing device is rather expensive.

Another type of prior art sensor is a semiconductor pressure sensor including an etched diaphragm and strain gauges. The entire sensor is inserted into a patient, thereby allowing the pressure sensing to take place at the point to be measured. Unfortunately, this prior art type of sensor is expensive and fragile, and requires electrical signals to be carried inside the patient in order to communicate with the sensor. This is particularly undesirable when measuring pressure within a coronary artery, due to the danger of fibrillation.

Yet another prior art pressure sensor utilizes optical fiber to transmit light to a membrane located at the tip of a catheter which is inserted into a patient to the desired location. The incident light transmitted by the optical fiber is reflected from the membrane as a function of that membrane's displacement due to the pressure being measured. The reflected light is then detected outside of the patient and the blood pressure being measured is electronically determined. These sensors measure absolute intensity of a reflected signal. Therefore they are subject to errors due to source intensity fluctuations, and microbend losses. Also, they cause errors due to changes in the mechanical structure and optical characteristics of the diaphragm due to vibrations, insertion damage, thermal expansions, etc.

Another type of prior art fiber optic pressure transducer is described by Lawson and Tekippe "Fiber-optic diaphragm-curvature pressure transducer", in *Optics Letters*, Vol. 8, No. 5, May 1983, pp. 286–288. This type of prior art fiber optic pressure transducer electronically detects the change in diaphragm curvature due to blood pressure, rather than diaphragm displacement. This sensor uses a bundle of fibers. As a result the diameter of the sensor is quite large. This makes it useless for intra-arterial sensing, particularly since often blood needs to be drawn through the same catheter or some other sensors may also be placed alongside the pressure sensor. The size of radial arteries is too small to accommodate such an arrangement with such a large sensor.

U.S. Pat. No. 4,270,050 describes a structure for measuring pressure by utilizing a pressure-sensitive optical modulator formed of a semiconductor, such as gallium arsenide, having a band gap which changes in proportion to pressure. This technology is not proven. Moreover, the resultant size is too large for intraarterial sensing.

All the above sensors are extremely difficult to manufacture as they require stringent tolerances on distances, etc.

Accordingly, there remains the need for a simple, disposable, low-cost in vivo pressure sensor which does not require the introduction of electrical signals within a patient.

SUMMARY OF THE INVENTION

In accordance with the teachings of this invention, a fiber optic pressure sensor suitable for use in measuring, for example, venous blood pressure, is taught. In accordance with this invention, a catheter tip is formed utilizing the phenomena of collision quenching or Foerster energy transfer quenching of fluorescence in order to measure the pressure exerted by the medium in which the sensors are placed. When utilizing a collision-quenching type of sensor constructed in accordance to the teachings of this invention, the change in concentration of a quencher is measured, the quencher being enclosed in the sensor tip, which is in hydrodynamic equilibrium with its ambient environment. Foerster-quenching type sensors constructed in accordance with the teachings of this invention measure the change in distance between the quencher and the fluorophore, which in turn are caused by pressure changes caused by the ambient environment in which the sensor is placed.

BRIEF DESCRIPTION OF THE DRAWINGS

FIG. 2b depicts the donor and acceptor matrix used in the embodiment of FIG. 2a.

DESCRIPTION OF SPECIFIC EMBODIMENTS

Figure 1:
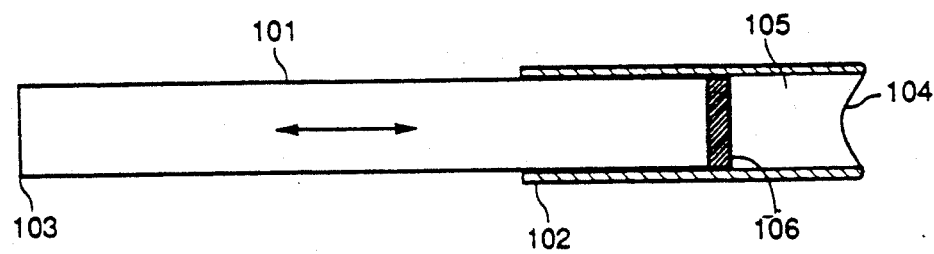
FIG. 1 is a cross-sectional view depicting one embodiment of a pressure sensor constructed in accordance with the teachings of this invention which relies on collision quenching.

FIG. 1 is a cross-sectional view depicting one embodiment of a pressure sensor constructed in accordance with the teachings of this invention, which relies on collision quenching of fluorescent chromophores. As is well known, fluorescent chromophores in the presence of certain molecules have a shortened excited-state lifetime and therefore decreased fluorescence intensity. This quenching depends on the collision probability between the chromophore and the quencher. Referring to FIG. 1, sensor 100 includes optical fiber 101, whose distal end 103 is coupled to electro-optic circuitry (not shown) for providing incident optical energy and for detecting the resultant optical energy. Optical fiber 101 is inserted into a patient such that flexible diaphragm 104 at the catheter tip is located at a desired point where pressure is to be measured. Cavity 105 is formed such that it is enclosed by rigid sleeve 102, optical fiber 101, and flexible gas tight membrane 104. In one embodiment, rigid sleeve 102 comprises a stainless steel tube.

Figure 4:
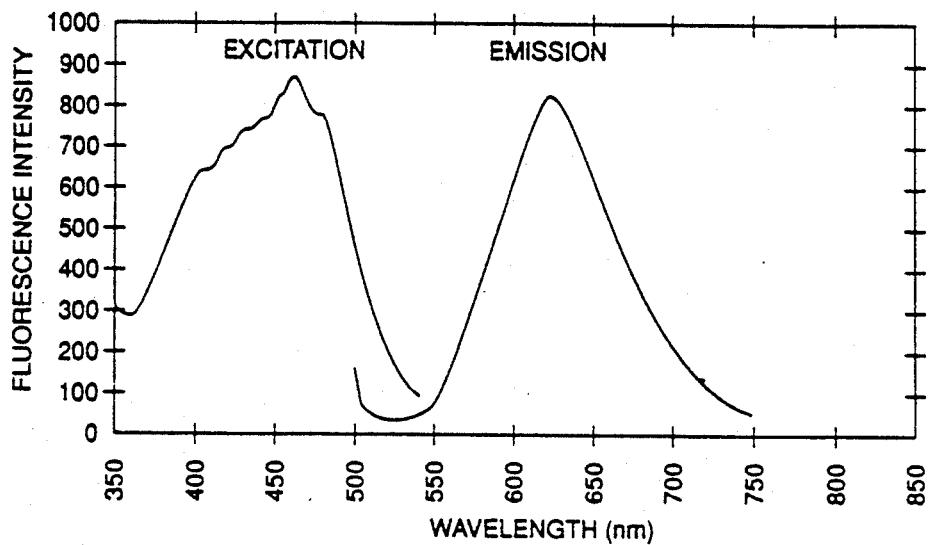
FIG. 4 depicts the excitation and emission spectra of the oxygen sensitive dye tris(4,7-diphenyl-1,10 phenanthroline) ruthenium II dichloride.
Figure 5:
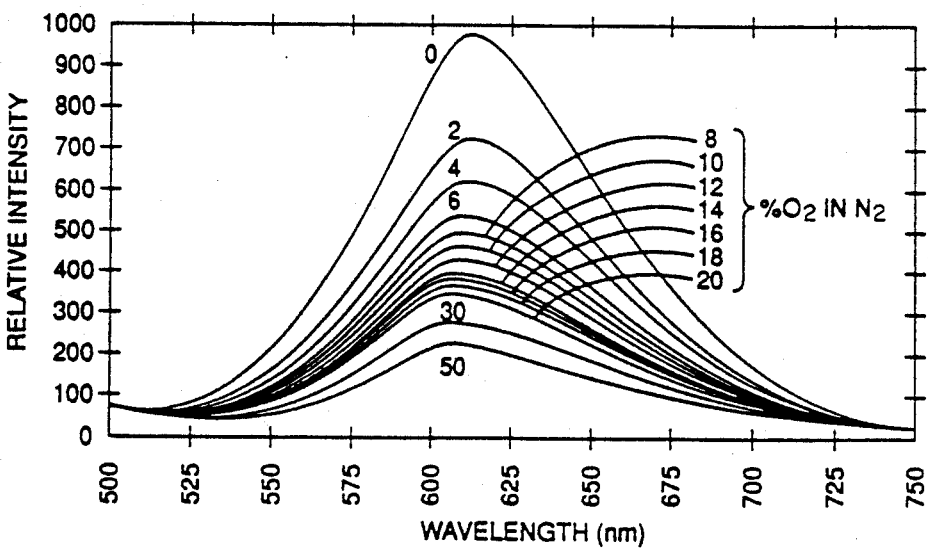
FIG. 5 depicts how the fluorescent intensity varies with oxygen concentration, with excitation energy at 450 nm.

Collision quenching type sensor 100 serves to measure the change in concentration of a quencher enclosed within region 105 which, due to flexible diaphragm 104, is in hydrodynamic equilibrium with its ambient environment. In one embodiment, the fluorophore contained within region 105 comprises an inorganic dye, such as tris(4,7-diphenyl-1,10 phenanthroline) ruthenium II dichloride ([Ru (Ph$_2$phen)$_3$]Cl$_2$ hereafter referred to as Ru(DIP)$_3^{2+}$ coated on the distal end of optical fiber 101, for example, in polymer matrix 106. FIG. 4 depicts the excitation and emission spectra of the oxygen sensitive dye such Ru(DIP)$_3^{2+}$. In such an embodiment, the quencher contained within region 105 comprises, for example, a gas mixture of nitrogen and oxygen. FIG. 5 depicts how the fluorescent intensity of Ru(DIP)$_3^{2+}$ varies with oxygen concentration, for an excitation energy of 450 nm. The oxygen and nitrogen components of the gas is established in a predetermined concentration and are contained within gas-tight region 105. The proportion of oxygen to nitrogen is preferably chosen such that the sensitivity of the sensor is maximized. This sensitivity is dependent upon the range of pressure measurement over which the sensor is to be used.

Figure 6:
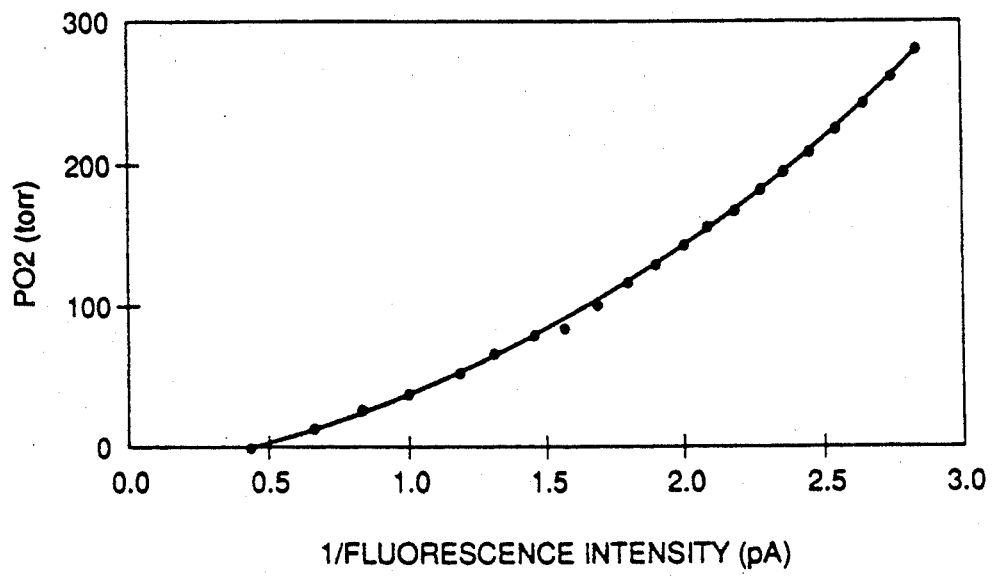
FIG. 6 is a graph depicting the partial pressure of oxygen as a function of reciprocal fluorescent intensity.

Changes in external pressure cause flexible diaphragm 104 to move, coupling the external pressure changes to region 105. This causes a change in the partial pressure of the oxygen and nitrogen quencher gas in sensor tip region 105, which then affects the collision probability of the nitrogen/oxygen quencher gas with the fluorophore. This, in turn, affects the intensity of fluorescence for a given amount of excitation energy. A measurement of the amount of flourecence provides an indication of extent of the collision quenching of the illuminated fluorophore, which is directly indicative of the pressure of the ambient environment in which sensor tip 105 is located. FIG. 6 is a graph depicting the partial pressure of oxygen measured as a function of reciprocal fluorescent intensity at the wavelength of peak excitation.

Thus, in operation, an ambient optical signal is transmitted from external circuitry (not shown) through optical fiber 101 to sensor tip 105. This ambient optical signal causes the fluorophore to fluoresce. The amount of fluorescence is related to the partial pressure which, as described above, causes an associated amount of quenching. The fluorescent emission is then coupled back through optical fiber 101 to external circuitry (not shown) for detection of its level. This is then correlated to the pressure existing at sensor tip 105.

Figure 2A:
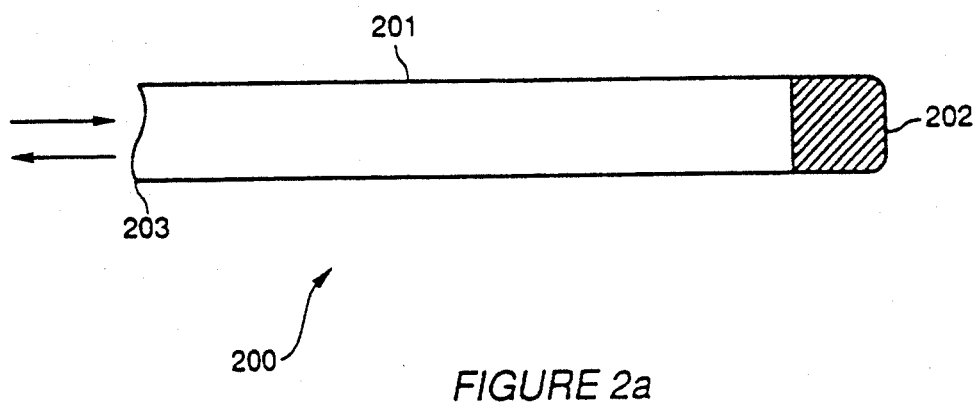
FIG. 2a is a cross-sectional view of another embodiment of a pressure sensor constructed in accordance with the teachings of this invention, which is based on Foerster quenching.

FIG. 2a depicts an alternative embodiment of this invention wherein a pressure sensor 200 is taught based on Foerster quenching. Sensor 200 includes optical fiber 201, having a proximal end 203 for coupling to an external source (not shown) of optical energy, and external detection circuitry (not shown). Tip 202 of sensor 200 relies on Foerster quenching, which depends on the mean distance between a chromophore and quencher. Foerster energy transfer occurs between fluorophores (donors) which have emission bands which overlap with the absorption band of quenchers (acceptors). This effect is due to a dipole-dipole interaction between donor and acceptor and varies as the sixth power of their separation, as is described by "Fluorescence Energy Transfer As a Spectroscopic Ruler" by L. Stryer in *Ann. Rev. Biochem.* (1978) 47:819–46. The energy transfer, and thus the quenching of the fluorophore, is thus very sensitive to the separation between the fluorophore and quencher. In accordance with the teachings of this invention, a pressure sensor is constructed wherein the ambient pressure is coupled to the sensor tip, thereby affecting the distance between donors and acceptors.

Figure 2B:
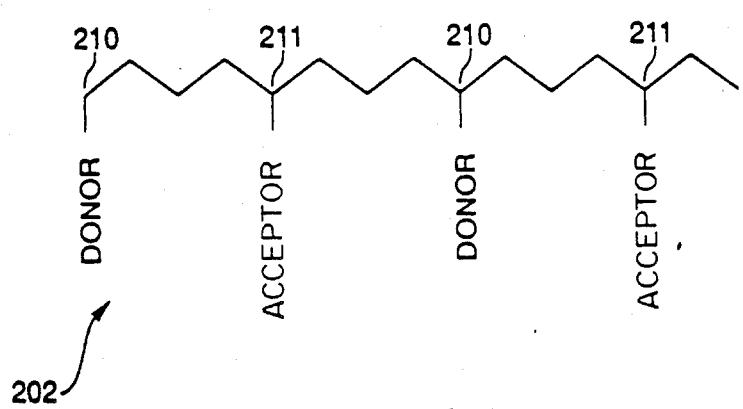

In one embodiment of this invention, an inorganic dye fluorophore is used, such as fluorescein, with a quencher, such as rhodamine 6G, as the emission spectra of fluorescein overlaps the absorption band of rhodamine 6G. In one embodiment, the fluorophore and quencher are immobilized in a compressible matrix placed at the distal end of optical fiber 201 and enclosed in a flexible gas-tight envelope 202. Such a compressible matrix is depicted in FIG. 2b with donors 210 and acceptors 211, located at specified locations within the compressible matrix. Such a matrix is composed of flexible polymer chains as shown in FIG. 2b. As the matrix is compressed or expanded the chains fold or extend thereby reducing or increasing the distance between the donor and the acceptor along the chain. Changes in external pressure cause changes in the volume of the foamy matrix, causing corresponding changes in the intramolecular separation of the fluorophores (donors 210) and quenchers (acceptors 211). The degree of quenching is thus a measure of the external pressure applied to sensor tip 202.

Figure 3:
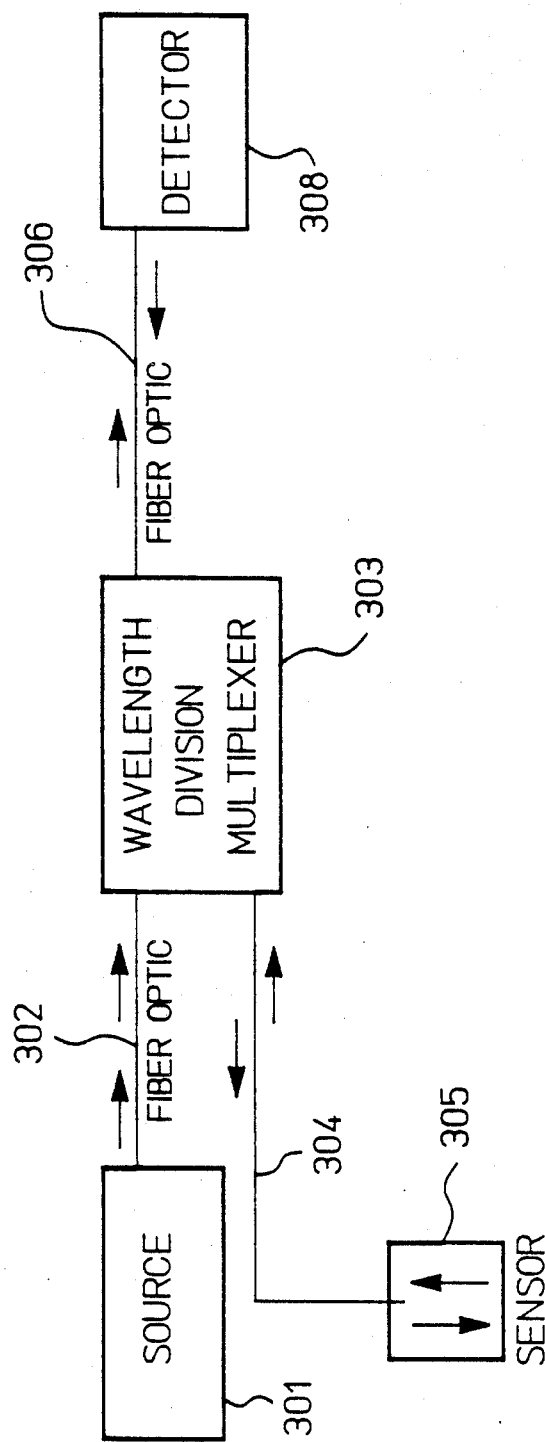
FIG. 3 is a block diagram depicting an instrument constructed in accordance with the teachings of this invention including a fiber optic pressure sensor.

FIG. 3 depicts one system constructed in accordance with the teachings of this invention for use with either the collision quenching-type sensor of FIG. 1 or the Foerster quenching-type sensor of FIG. 2. As shown in FIG. 3, optical source 301 provides excitation optical energy on optical fiber 302 to wavelength division multiplexer 303. This excitation optical energy is coupled to optical fiber 304 to sensor 305. This excitation optical energy causes fluorescence within sensor 305, which fluorescence is partially quenched by collision-quenching mechanism (as described above, with regard to FIG. 1) or a Foerster-type quenching mechanism (as described above with reference to the embodiment of FIG. 2). The fluorescent energy is coupled from sensor 305 through optical fiber 304 to wavelength division multiplexer 303. Wavelength division multiplexer 303 directs this returning fluorescence optical signal, which has a wavelength different than the wavelength of excitation optical energy provided by optical source 301 to the detector 307. The returning optical energy is then converted to an electronic signal by the detector 307, and a determination made regarding the intensity of the fluorescent energy, which in turn is an indication of the pressure detected by sensor 305.

Figure 7:
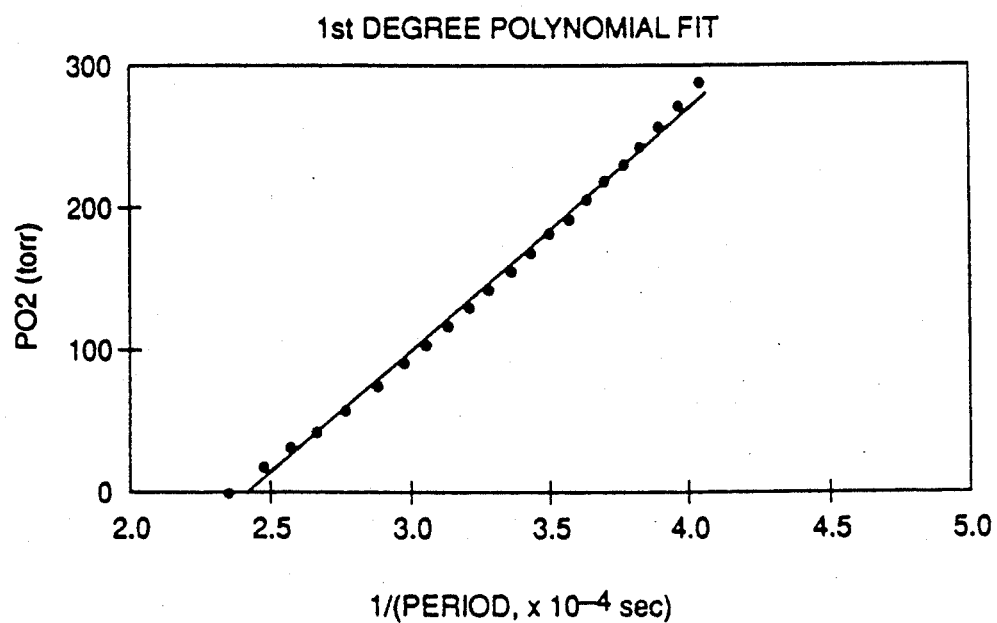
FIG. 7 is a graph depicting the period derived from the fluorescent decay curve, as derived from a frequency domain measurement of the fluorescent energy.

In accordance with the teachings of this invention, a frequency domain or time domain approach is used to measure the pressure detected by sensor 305. This involves using either pulsed or sinusoidally modulated excitation light. The degree of quenching is then a function of the decay time or phase shift of the fluorophore emission. FIG. 7 is a graph depicting the period derived from the fluorescent decay curve, as derived from a frequency domain measurement of the fluorescent energy. Utilizing a frequency or time domain approach greatly simplifies or completely eliminates requirements for a reference signal, as variations in the intensity of the optical signal provided by optical source 301, losses due to optical fiber bending and connectors do not affect the decay time or phase shift of the fluorescence.

Another advantage provided in accordance with the teachings of this invention is that excitation energy and returning energy from the sensor tip have different wavelengths in accordance with the fluorescence phenomenon, thereby simplifying directional coupling for single fiber systems. This eliminates the difficulty of attempting to sense a returning signal having the same wavelength as the excitation signal, as is the case in prior art optical fiber pressure sensor systems.

Furthermore, unlike prior art optical fiber pressure sensors, the determination of the pressure is based on a quantum mechanical phenomena, rather than a mechanical phenomena such as deflection or displacement of a diaphragm. This leads to the ability to provide a sensor tip in accordance with the teachings of this invention which is significantly smaller than possible with the teachings of the prior art. Furthermore, since the quantum mechanical phenomena utilized in accordance with the teachings of this invention is intrinsic to the material located at the sensor tip, the optical signal representative of the pressure detected by the sensor is not dependent upon the shape of the sensor tip, as is the case with prior art sensors which detect movement of a diaphragm or change in the curvature of a diaphragm. Thus, a sensor is taught which obviates the need for high precision machining, as is necessary in the prior art.

Yet another advantage of this invention is that the pressure associated with the operating point, as well as the sensitivity to changes in pressure from this operating point, can be tailored as needed simply by selecting appropriate types and concentrations of fluorophore and quencher.

The invention now being fully described, it will be apparent to one of ordinary skill in the art that many changes and modifications can be made thereto without departing from the spirit or scope of the appended claims.

What is claimed is:

1. A pressure sensor comprising:
   a sample region hydrostatically coupled to a region from which pressure is to be measured, said sample region being at least partially enclosed by a gas tight flexible membrane for coupling the pressure of said region to be measured to said sample region;
   an optical fiber for coupling excitation energy to said sample region;
   an optical fiber for coupling fluorescent energy from said sample region;
   one or more fluorescent chromophores located within said sample region, said chromophores providing said fluorescent energy in response to said excitation energy; and
   quenching molecules located within said sample region, said quenching molecules causing said fluorescent chromophores to have a shortened excited-state lifetime.

2. A sensor as in claim 1 wherein said optical fibers comprise a single optical fiber.

3. A sensor as in claim 1 wherein said fluorescent chromophores comprise an inorganic dye.

4. A sensor as in claim 3 wherein said flourescent chromophores comprise tris(4,7-diphenyl-1,10 Phenanthroline) ruthenium II dichloride and said quenching molecules comprise oxygen and nitrogen gas.

5. A sensor as in claim 1 which further comprises a polymer matrix upon which said flourescent chromophores are coated.

6. A sensor as in claim 5 wherein said polymer matrix is located at the end of said optical fiber located in said sample region.

7. A pressure sensor system comprising:
   means for providing excitation optical energy;
   means for coupling said excitation optical energy to a sample region;
   means for at least partially enclosing said sample region by a gas tight flexible membrane for coupling the pressure of a region to be measured to said sample region;
   means, located within said sample region, for generating fluorescent energy in response to said excitation energy;
   means, located within said sample region, for quenching the generation of at least a portion of said fluorescent energy;
   detection means for detecting said fluorescent energy and determining the pressure in said sample region in response thereto; and
   means for coupling said fluorescent energy to said detection means.

8. A method for determining pressure in a sample region comprising the steps of:
   coupling the pressure of a region to be measured to said sample region by at least partially enclosing said sample region by a gas tight flexible membrane;
   coupling excitation optical energy to said sample region;
   causing fluorescent energy to be generated in response to said excitation optical energy;
   causing said generation of said fluorescent energy to be at least partially quenched in response to pressure in said sample region; and
   detecting said fluorescent energy and making a determination of the pressure in said sample region in response thereto.

* * * * *